United States Patent [19]

Schoneman

[11] 3,999,863
[45] Dec. 28, 1976

[54] APPARATUS FOR MEASURING LIGHT ABSORPTION
[75] Inventor: Charles R. Schoneman, Riverside, Calif.
[73] Assignee: Rohr Industries, Inc., Chula Vista, Calif.
[22] Filed: Aug. 13, 1975
[21] Appl. No.: 604,199
[52] U.S. Cl. .................................. 356/201; 356/202
[51] Int. Cl.² ......................................... G01N 21/22
[58] Field of Search .......... 350/271; 356/184, 186, 356/201, 202

[56] References Cited
UNITED STATES PATENTS

| | | | |
|---|---|---|---|
| 2,206,214 | 7/1940 | Wicker | 356/201 |
| 3,627,431 | 12/1971 | Komarniski | 356/201 |
| 3,685,885 | 8/1972 | Scott | 350/271 |
| 3,761,184 | 9/1973 | McLaughlin, Jr. | 356/186 |
| 3,910,701 | 10/1975 | Henderson et al. | 356/201 |

Primary Examiner—Vincent P. McGraw
Attorney, Agent, or Firm—Patrick J. Schlesinger; Frank D. Gilliam

[57] ABSTRACT

An open area photometer for determining the amount of light energy dissipated when a light source of known intensity is passed through a light restricting test specimen. The photometer includes a light source whose intensity level is established by an adjustable shutter positioned in front of the light source, a light diffusing element positioned between the shutter and a fresnel lens, a field effect phototransistor whose output is monitored on a micro-ammeter and a housing confining the components to prevent unwanted light loss. The specimen is positioned between the lens and the light diffusing element.

9 Claims, 6 Drawing Figures

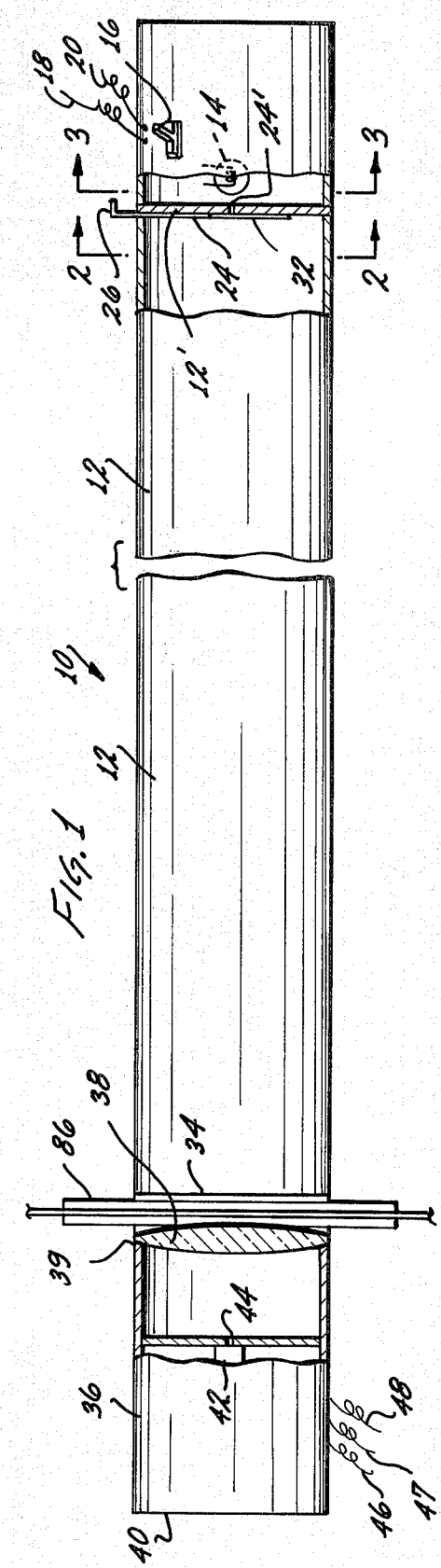
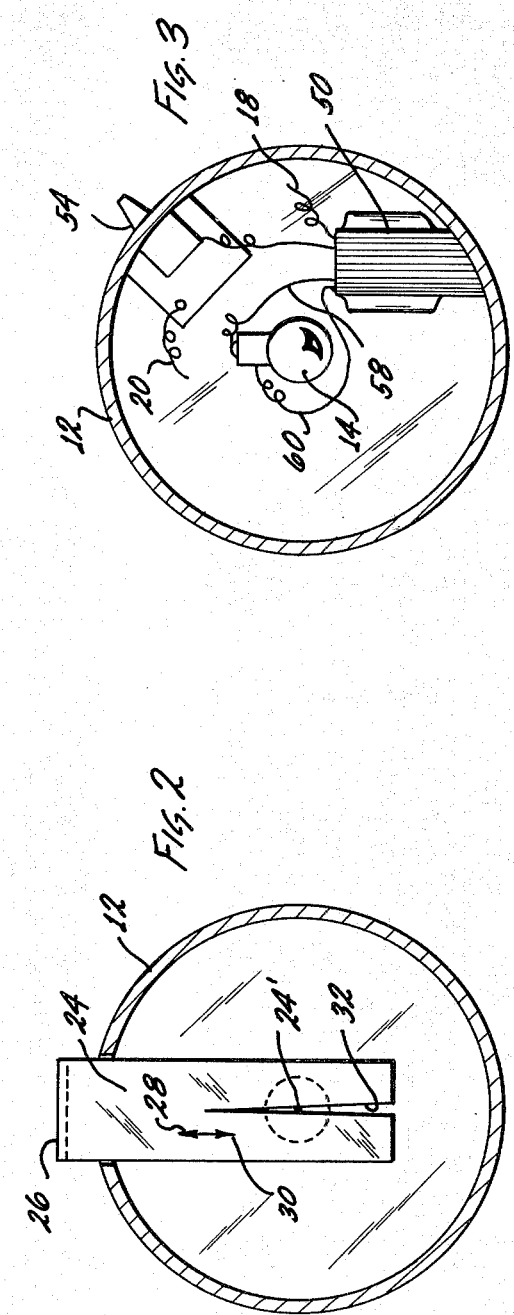

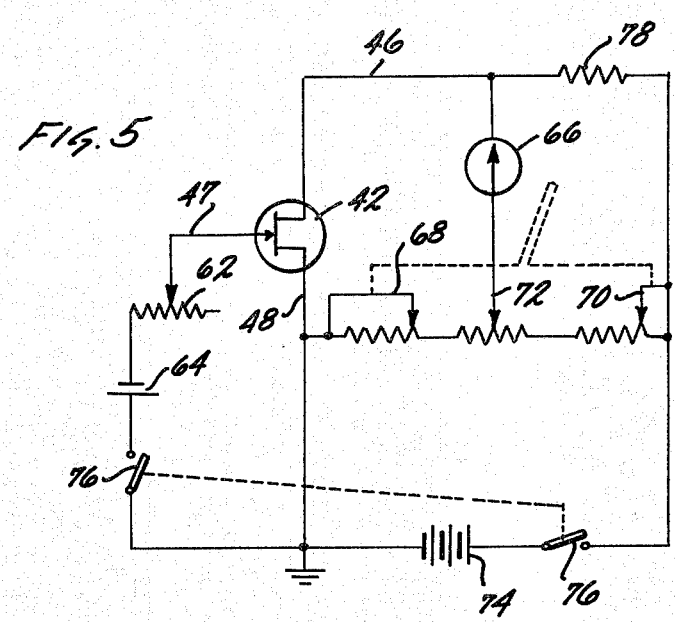
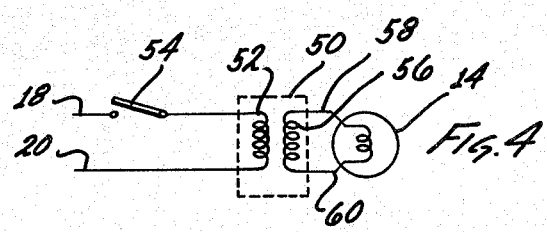
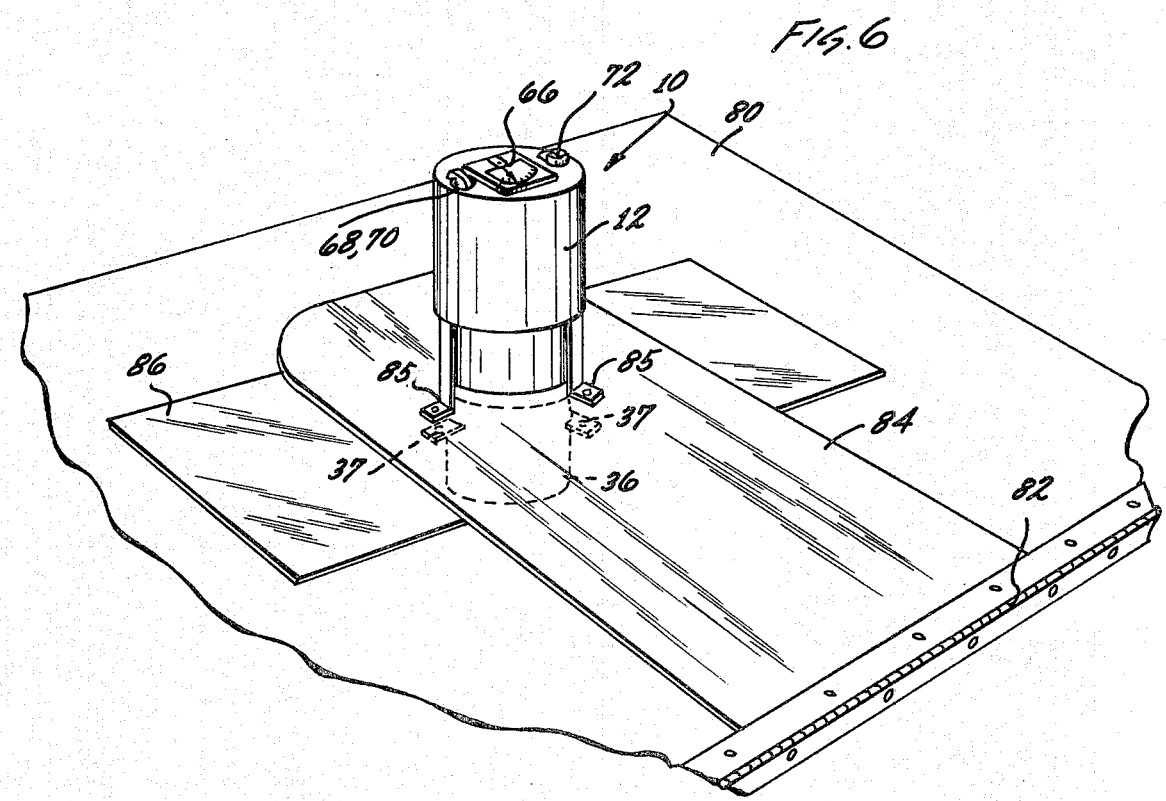

APPARATUS FOR MEASURING LIGHT ABSORPTION

BACKGROUND OF THE INVENTION

The invention is in the field of optical scanning instruments employed for assessing the uniformity of perforated sheets, sheets of paper, plastics, glass and the like.

The measurements of the degree of light transmission through sheets of material, such as, perforated sheets where the light restriction characteristics are a function of the number and size of the perforations or the degree of transparency of paper, plastic, glass and the like, and particularly the measurement of localized variability in light transmission as an assessment of uniformity, has frequently been proposed in the past.

A number of instruments are available for the purpose and methods and are well developed for interpreting parameters of variations in terms of light level and the fluctuating component. It is usual practice to connect the light signal to an electrical output signal and to measure amplitude of the output signal.

The instruments generally comprise a system of illuminating the test sheet by a small light spot produced by an appropriate combination of lenses, a light-gathering system of lenses to focus the transmitted light on a photomultiplier as a light sensing element, a regulated D.C. power supply for the photomultiplier and illuminating source and electronic amplification and monitoring equipment. In general, the equipment is complex, expensive and can test only a small surface area with each test, three disadvantages which have limited their application to laboratory use.

SUMMARY OF THE INVENTION

The present invention provides an apparatus for uniform measurement of sheet material which is simple, reliable and produced at low economic cost.

The invention resides in the unique concept of comparing a standard specimen of material with a specimen of the same material of unknown quality. The standard specimen is placed into test position and a level of light penetration is established by the light sensor. When the level of penetration of the known sample is established, a similar piece of material with unknown light penetration qualities is placed in position in the same manner as before, and its light penetration level is checked. If the level of the test specimen is substantially the same as the standard, the specimen is passed and if the test level is substantially different, the test sample is rejected.

Other advantages of this invention will become more apparent when taken in conjunction with the drawings in which:

BRIEF DESCRIPTION OF THE DRAWINGS

FIG. 1 is a partial side view of the apparatus in accordance with the invention.

FIG. 2 is a portion of FIG. 1 taken along line 2—2.

FIG. 3 is a portion of FIG. 1 taken along line 2—2.

FIG. 4 is a partial showing circuit of the light source.

FIG. 5 is a schematic diagram of the electrical circuit of the light sensing system.

FIG. 6 is a showing of the apparatus mounted for typical use.

DESCRIPTION OF THE PREFERRED EMBODIMENT

Referring now to FIG. 1. The photometer 10 is shown with an elongated housing 12. This housing is generally circular in cross-section for ease of conforming parts, however, different shapes may be used to practice the invention. Confined within the housing 12 is a light source 14 having an external control switch 16 wired to a suitable power source through wires 18, 20. A wall 22 having a pin hole 24 there through separates the light source 14 from shutter 24.

As can be best seen in FIG. 2, shutter 24 has an external handle 26 for manually moving the direction of the shutter 24 in and out along arrows 28, 30, the housing 12 so that the light from pin hole 24 can be controlled as to intensity passing through slot 32. The shutter is firmly held in the slot through housing 12 by friction.

The light leaving slot 32 is confined within the housing walls and is effectively collimated to the light diffuser 34 at the end of the housing. The light diffuser 34 in the preferred embodiment is formed of tissue paper across the opening at the end of the housing 12. Any suitable translucent material such as plastic, etched glass and the like, may be utilized equally as well to practice the invention.

Referring again to FIG. 1, a second housing 36 of the same diameter as housing 12 is shown on FIG. 1. This housing has a fresnel lens 38 mounted at one end 39. The opposite end 40 is enclosed. Intermediate to the ends 39, 40 is a photo-field effect transistor 42 with its light sensitive area 44 positioned in the center of the housing facing the fresnel lens 38. Electrical leads 46, 47 and 48 from transistor 42 are connected as shown in FIG. 5.

Referring now to FIGS. 3 and 4, the electrical circuit for the lamp 14 is shown. The power supply shown, as an example, is a stepdown transformer 50 that has primary 52 attached to ordinary household current through switch 54 by lead wires 18, 20. The secondary 56 is attached to lamp 14 of a voltage reduced from the primary level through lead wires 58, 60. Any convenient power source may be used equally as well to practice the invention.

Referring now to FIG. 5, a wiring diagram for the photo-field effect transistor 42 is shown. The photo-field transistor is a type FF103, manufactured by Cryetalonics, or equivalent. The gain of transistor 42 is set by adjusting adjustable resistor 62 which supplies current from low voltage power supply 64. Meter 66 is typically a 0-100 DC micro-ammeter. The current output of transistor 42 can be adjusted by dual ganged variable resistors 68, 70. The meter 66 is zero adjusted by variable resistor 72. The meter circuit is powered by voltage supply 74. The transistor gain circuit and the meter circuit are energized by single throw double pole switch 76. The ground for power supplies 64, 74 are common.

The power supplies 64, 74 are typically 1.5V DC and 9V DC, respectively. The gain resistor 62 is approximately 2 Meg ohms. Resistor 72 is a 2K ohm wire wound resistor and resistors 68, 70 are each 10K ohms. A 1K ohm current limiting resistor 78 is also shown in FIG. 5.

FIG. 6 shows a typical means for mounting the apparatus for production use. A table 80 having a hole in its center upper surface of sufficient size to fixedly mount housing 36 by brackets 27 with the fresnel lens 38 facing upward. A hinged member 82 mounts plate 84 to the table edge as shown. Mounted on the plate 84 by brackets 85 is housing 12 with the diffuser 34 adjacent the lens 38. The two housings 12, 36 are in co-axial alignment. A test specimen 86 positioned between the table top and the underside of plate 84 is shown in test position. It can be clearly seen that the plate 84 can be hinged upward for various thicknesses of test specimens or for the positioning of test specimens.

OPERATION OF THE PREFERRED EMBODIMENT

A short explanation of the operation principles and manner of use is hereinafter explained.

The apparatus operates in the following manner. When the power is energized the illumination from the lamp passes through a pin hole where it is then adjusted to a selected intensity level by the manipulation of the shutter. The light is then collimated by the inside housing boundaries which are sealed to the exterior. This collimated light is then diffused by a diffusing means placed in its path. This diffused light then passes through a fresnel lens which focuses the diffused light which strikes the receiving surface of the photo-field effect transistor which in turn provides an electrical signal output related to the intensity of the focused light. This output is then monitored by the microammeter for light intensity. The focal length between the fresnel lens and the photo-field effect transistor is such that the light beam diameter at the receiving surface of the photo-field effect transistor is slightly larger than the receiving surface of the transistor.

Assuming that the meter has a proper zero preadjusted, the switch 76 is closed allowing current to flow through all portions of the detectors electronic circuits. The operator then inserts a piece of material of known light restricting quality, for example, when perforated material is being tested, a sample of material having a known number of a specific size openings per square inch, the meter is then viewed and its indicating needle is set for a convenient position, typically center scale would be chosen so that plus or minus readings could be utilized as required. The standard or known quality sample is then removed and a piece of similar material of unknown quality is tested in the same manner without further adjustment of the various controls. The operator then notes the needle position while passing various portions of the material through the apparatus. Center scale indicating production specimens would be considered the same or similar to the test standard and would be acceptable as would test samples within established plus or minus parameters around the ideal zero reading. Test samples falling outside of the established tolerance parameters would be rejected as not comparable to the standard specimen as to light restricting or passing qualities.

Variations and modifications may be made within the scope of the invention, and portions of the improvements may be used without others.

I claim:

1. An open area photometer for determining the degree of light passing through at least a selected portion of a light restraining test sample comprising, a first portion, said first portion comprises an enclosed chamber at one end thereof for housing a source of light and a diffusion means positioned adjacent said test sample at the other end thereof, the wall of said enclosed chamber intermediate the end of said first portion has a pin hole aperture therethrough for passing light from said source, light intensity adjusting means is positioned between said pin hole aperture and said diffusion means and a second portion spaced the width of said test sample from the diffusion means end of said first portion positioned co-axial therewith, said second portion comprises a closed chamber with an opening in the end adjacent said test sample, means for focusing said light after passing through said opening and means positioned between said light focusing means and the other end of said closed chamber of said second means, for measuring the intensity of the diffused light after passing through said test sample.

2. The invention as defined in claim 1, wherein said light source intensity is adjustable by a mechanical shutter having a slot therethrough positioned between said light source and said diffusing means.

3. The invention as defined in claim 2, wherein said slot is V-shaped.

4. The invention as defined in claim 1, wherein said means for diffusing is constructed of translucent material.

5. The invention as defined in claim 1, wherein said focusing means is a fresnel lens.

6. The invention as defined in claim 1, wherein said means for measuring said diffused light is a light sensor.

7. The invention as defined in claim 6, wherein said light sensor is a field effect phototransistor.

8. The invention as defined in claim 7, wherein said light sensor additionally comprises a meter movement for reading the output of said field effect phototransistor.

9. The invention as defined in claim 1, wherein said first portion is attached to a work surface by a hinged member extending from the outer edge of said work surface to the central portion thereof, said work surface includes an aperture therethrough, said second portion is fixedly attached to the underside of said work surface, said aperture in said work surface is substantially co-axial with said second portion and is co-axial with said first portion when said first portion is in an operational position.

* * * * *